(12) United States Patent
Jeglorz et al.

(10) Patent No.: US 9,301,877 B2
(45) Date of Patent: Apr. 5, 2016

(54) DEVICE FOR ASSISTING IN THE PREPARATION OF AN OPERATION ON THE HUMAN EYE

(75) Inventors: Tobias Jeglorz, Nuremberg (DE); Christof Donitzky, Eckental (DE)

(73) Assignee: Wavelight GmbH (DE)

( * ) Notice: Subject to any disclaimer, the term of this patent is extended or adjusted under 35 U.S.C. 154(b) by 128 days.

(21) Appl. No.: 14/234,532

(22) PCT Filed: Jul. 28, 2011

(86) PCT No.: PCT/EP2011/003802
§ 371 (c)(1),
(2), (4) Date: Jan. 23, 2014

(87) PCT Pub. No.: WO2013/013690
PCT Pub. Date: Jan. 31, 2013

(65) Prior Publication Data
US 2014/0142599 A1    May 22, 2014

(51) Int. Cl.
*A61F 9/008* (2006.01)
*A61F 9/009* (2006.01)
*A61F 9/013* (2006.01)

(52) U.S. Cl.
CPC .............. *A61F 9/00836* (2013.01); *A61F 9/009* (2013.01); *A61F 9/0133* (2013.01); *A61F 2009/00872* (2013.01); *A61F 2009/00878* (2013.01)

(58) Field of Classification Search
CPC .................. A61F 2009/00872; A61F 9/00836; A61F 2009/0088; A61F 2009/00882
See application file for complete search history.

(56) References Cited

U.S. PATENT DOCUMENTS

2002/0115988 A1 * 8/2002 Holladay ......................... 606/5
2003/0133074 A1 * 7/2003 Pettit et al. .................... 351/212
(Continued)

FOREIGN PATENT DOCUMENTS

| CN | 1781466 | 6/2006 |
| CN | 1781466 A | 6/2006 |

(Continued)

OTHER PUBLICATIONS

Bob Kronemyer; Smaller suction ring of Moria keratome works for shallow orbits of Asian eyes; Healio; Ocular Surgery News U.S. Edition; Nov. 15, 2000.
(Continued)

*Primary Examiner* — Khoi Tran
*Assistant Examiner* — Ryan Rink (57) ABSTRACT

According to an exemplary embodiment, a device (12) for assisting in the preparation of an operation on the human eye (14) for the purpose of generating a corneal flap by means of a microkeratome system (10) includes: an input interface arrangement (50) that permits at least the input of data relating to a set value of at least one flap parameter and also to at least one patient-related parameter; a computer (46) that has been set up to access a stored data collection (44) of several surgical data records, each of which includes a post-operative actual value of at least one flap parameter, a value for at least one patient-related parameter and configuration data of the microkeratome system, the computer (46) having been set up to ascertain, on the basis of the data collection (44) in a manner depending on the input data, configuration information that represents a proposed configuration of the microkeratome system (10); an output interface arrangement (48) for outputting the configuration information.

17 Claims, 5 Drawing Sheets

(56) References Cited

U.S. PATENT DOCUMENTS

| | | |
|---|---|---|
| 2004/0002697 A1* | 1/2004 | Youssefi et al. .................... 606/5 |
| 2006/0064121 A1* | 3/2006 | Sempe .......................... 606/166 |
| 2007/0027439 A1 | 2/2007 | Durrie et al. |
| 2007/0255297 A1* | 11/2007 | Sempe .......................... 606/166 |
| 2009/0247997 A1 | 10/2009 | Watanabe et al. |
| 2009/0257065 A1 | 10/2009 | Hauger et al. |
| 2010/0324542 A1 | 12/2010 | Kurtz |
| 2011/0202044 A1 | 8/2011 | Goldshleger et al. |
| 2011/0224657 A1* | 9/2011 | Stevens et al. .................... 606/5 |
| 2012/0092615 A1 | 4/2012 | Izatt et al. |
| 2013/0141695 A1 | 6/2013 | Buckland et al. |

FOREIGN PATENT DOCUMENTS

| | | |
|---|---|---|
| EP | 1757253 A1 | 2/2007 |
| JP | 2004538088 | 12/2004 |
| JP | 2006522671 | 10/2006 |
| WO | 2011035063 A1 | 3/2011 |
| WO | 2012166116 A1 | 12/2012 |

OTHER PUBLICATIONS

International Search Report and Written Opinion issued for PCT/US2014/071153, dated Mar. 31, 2015, 11 pgs.

\* cited by examiner

① Desired target values: flap thickness 120 μm +/-10,   flap diameter 9,3 mm +/- 0,1, hinge 4,5 mm +/- 0,1
   (tolerance bands saved in the software)

② Look up which combinations come closest to the desired values

Data pool

| Cutting head | Suction ring | Vacuum | Oscillation | IOP | K-value | Pachy | Flap thickness | Flap diameter | Hinge | Age |
|---|---|---|---|---|---|---|---|---|---|---|
| A | A | 450 | 8000 | 23 | 42,5 | 456 | 113 | 9,3 | 4,6 | 32 |
| B | B | 550 | 8000 | 20 | 41,3 | 506 | 135 | 8,3 | 4,3 | 46 |
| C | A | 550 | 8000 | 19 | 43,5 | 480 | 140 | 9,3 | 5,2 | 25 |
| B | A | 550 | 8000 | 20 | 39,3 | 510 | 125 | 9,4 | 4,2 | 39 |
| A | A | 450 | 8000 | 21 | 42,0 | 503 | 118 | 9,2 | 4,4 | 19 |

③ Extract and group the data

| Cutting head | Suction ring | Vacuum | Oscillation | IOP | K-value | Pachy | Flap thickness | Flap diameter | Hinge | Age | |
|---|---|---|---|---|---|---|---|---|---|---|---|
| A | A | 450 | 8000 | 23 | 42,5 | 456 | 113 | 9,3 | 4,6 | 32 | Group 1 |
| A | A | 450 | 8000 | 21 | 42,0 | 503 | 118 | 9,2 | 4,4 | 19 | |
| B | A | 550 | 8000 | 20 | 39,3 | 510 | 125 | 9,4 | 4,2 | 39 | Group 2 |

FIG. 3b

④ Take the combination in which the values cluster

| Cutting head | Suction ring | Vacuum | Oscillation | IOP | K-value | Pachy | Flap thickness | Flap diameter | Hinge | Age |
|---|---|---|---|---|---|---|---|---|---|---|
| A | A | 450 | 8000 | 23 | 42,5 | 456 | 113 | 9,3 | 4,6 | 32 |
| A | A | 450 | 8000 | 21 | 42,0 | 503 | 118 | 9,2 | 4,4 | 19 |

⑤ Averaging of the values

| Cutting head | Suction ring | Vacuum | Oscillation | IOP | K-value | Pachy | Flap thickness | Flap diameter | Hinge | Age | |
|---|---|---|---|---|---|---|---|---|---|---|---|
| A | A | 450 | 8000 | 22 | 42,25 | 479,5 | 115,5 | 9,25 | 4,5 | 25,5 | Mean value |
|  |  | 0 | 0 | 1,41 | 0,35 | 33,23 | 3,54 | 0,07 | 0,14 | 9,2 | Standard deviation |

⑥ Proposal of the ascertained combination and settings

Cutting head A, Suction ring A, Vacuum 450 mmHg, Oscillation 8000 $s^{-1}$, Hinge 4,5 mm

Evaluation in the dependency diagram

DEVICE FOR ASSISTING IN THE PREPARATION OF AN OPERATION ON THE HUMAN EYE

CROSS REFERENCE TO RELATED APPLICATIONS

This application is a section 371 national stage phase of International Application No. PCT/EP2011/003802, filed 28 Jul. 2011, titled "DEVICE FOR ASSISTING IN THE PREPARATION OF AN OPERATION ON THE HUMAN EYE," which is hereby incorporated by reference in its entirety.

The invention concerns the field of eye-surgery treatments, in particular the field of LASIK operations on the human eye.

'LASIK' stands for laser in-situ keratomileusis. It is a surgical technique, in the course of which a flap is firstly prepared which is then folded aside in order to expose the underlying regions of the corneal tissue. The exposed tissue is then treated in ablating manner by means of UV laser radiation. In the course of the ablation, corneal material is resected in accordance with an ablation profile previously ascertained for the patient. After laser treatment has taken place, the flap is folded back again. As a consequence of the previous resection of material, an altered shape of the anterior surface of the eye becomes apparent. Associated with this, the refractive behaviour of the cornea changes—i.e. the imaging properties of the overall system constituted by the eye are changed. Cases of defective vision—such as, for example, short-sightedness, long-sightedness or astigmatism—may in this way be at least alleviated or at best completely eliminated.

Various techniques are known in the professional field for the generation of the flap. One technique uses a microkeratome—i.e. a microsurgical scalpel with which the flap is cut mechanically. Another technique employs short-pulse laser radiation (for example, with pulse durations within the nanosecond, picosecond, femtosecond or even attosecond range), with which it is possible to make intra-tissue incisions by juxtaposition of a large number of photodisruptions, each generated locally. Such photodisruptions arise as a consequence of a laser-induced dielectric breakdown in the material of the human cornea, which is transparent to the laser radiation.

Within the scope of the invention, both the generation of the flap by means of a mechanical microkeratome and the generation of the flap by means of laser radiation will be considered. Even though there are numerous varying designs of microkeratome—which differ, inter alia, by virtue of, for example, the shape and the course of motion of a cutting blade (cutting knife) that is used for cutting the flap—a factor that is common to at least most of the microkeratomes is that they require a suction ring to be mounted onto the eye, which is fixed to the eye by reduced pressure and which serves for guiding or/and supporting a cutting head bearing the cutting blade. The cutting head is frequently part of a handpiece which includes, in addition to the cutting head, a motorised drive unit for driving the cutting blade. The suction ring may be a component that is separate from this handpiece and that is firstly fixed to the eye before the handpiece comes into operation. Also conceivable is a construction of the suction ring as a modular unit with the cutting head and the drive unit.

The handpiece is ordinarily connected via one or more electrical cables to a control console which, for example, is constructed as a bench instrument and which contains the necessary electrical and electronic components for supplying the operating voltage of the drive unit and for controlling it. Frequently a vacuum-pump arrangement is also accommodated in the control console, which generates the vacuum needed for the suction fixation of the suction ring to the eye of the patient. The suction ring may accordingly be capable of being connected to the control console via one or more hose lines.

A suction ring of such a type (with assigned controllable vacuum-pump arrangement) also finds application, as a rule, in the case of laser-assisted flap preparation, in order to keep the eye of the patient open during the laser machining. In this case the suction ring may constitute at the same time a mechanical interface for a patient adapter which is coupled (where appropriate, detachably) to a housing component of the laser system being used and which may exhibit a contact element, transparent to the laser radiation, for abutment against the eye. This contact element may have been constructed with a plane or otherwise shaped contact face which the surface of the eye conforms to in planar manner, in order in this way to enable a precise referencing of the eye in the coordinate system of the laser. Exemplary designs of a suction ring and of a patient adapter for application in the course of the generation of incisions in the human eye by laser technology (in particular for the purpose of flap preparation) are shown in WO 2010/022745 A1 and WO 2008/110368 A1.

By the term 'flap-preparation system' which is used here, the totality of the components that are required in order to cut a corneal flap is understood (inclusive of a control unit, for example in the form of a bench instrument). An exemplary mechanical flap-preparation system (i.e. a microkeratome system) possesses a cutting blade with a rectilinear cutting edge which is set in lateral oscillation at high frequency while, at the same time, a cutting head with the cutting blade oscillating therein is pushed forward in rectilinear manner. Similar microkeratome systems are shown and described in EP 1 752 120 A1 and also in EP 1 757 253 A1.

The flap is a circular, elliptical or otherwise shaped covering disc which is not completely severed from the remaining corneal tissue but is still connected to the remaining corneal tissue in a hinge region. Depending on the patient and the treatment, it may be necessary to prepare the flap with varying dimensions. For example, the flap diameter, the flap thickness, the marginal-incision angle of the flap and values for dimension or/and position of the hinge edge are suitable as characteristic dimensions. A hinge dimension is, for example, the hinge length. A hinge position is, for example, the hinge location, expressed as the location of the hinge edge relative to the circular peripheral line of the flap. This location may, for example, be expressed by a spacing dimension, namely the spacing of the hinge edge from a tangent, parallel to the hinge edge, of the circular peripheral line of the flap. In the case of a microkeratome system with a cutting head that is capable of being pushed forward in rectilinear manner the hinge location may be defined, for example, by the feed distance of the cutting head. In many designs of a microkeratome system the user can freely preset a desired feed distance and hence a desired hinge location; a control unit of the microkeratome system then ensures that the cutting head stops after travelling the set feed distance and travels back again.

Before the flap is generated the operating surgeon has to determine desired values for the characteristic parameters of the flap and configure the flap-preparation system accordingly. Numerous manufacturers of flap-preparation systems offer varying types, at least for individual system components. For example, a manufacturer of mechanical flap-preparation systems may offer for varying thicknesses of the flap varying cutting heads which differ, for example, by virtue of the extent by which the cutting edge of the cutting blade protrudes downwards in relation to an applanation face of the cutting head. This extent determines the depth of the incision and hence the thickness of the flap. In this way a certain nominal incision depth may have been assigned to each cutting head, this nominal incision depth also being designated within the scope of the present disclosure as the size of the cutting head.

A manufacturer of a flap-preparation system may also offer suction rings in varying sizes, each suction ring having a different inside diameter. In the mechanical variant of flap preparation the inside diameter of the suction ring ordinarily determines the diameter of the flap, so that each suction ring corresponds to a certain nominal flap diameter.

In clinical practice it has become evident that the results actually achieved do not always match the desired flap dimensions. If in the case of a mechanical flap-preparation system the operating surgeon chooses, for example, a suction ring with a size (inside diameter) of 9 mm and a cutting head with a size (nominal incision depth) of 120 μm, this does not mean that the flap actually generated always exhibits exactly the same dimensions. Instead of this, more or less considerable deviations between the actual flap dimensions and the nominal dimensions of the suction ring and of the cutting head may arise. In this connection it is frequently the case that a number of different factors are responsible for these deviations, whereby as a rule it is not possible for the operating surgeon to predict precisely, solely from his/her wealth of experience, how the actual flap dimensions will be in a particular configuration of the flap-preparation system.

In particular, it has become evident that the deviations between a desired target value of a flap dimension and the actual value of this flap dimension achieved post-operatively can be influenced by a number of patient-specific, instrument-specific or/and operating-surgeon-specific boundary conditions. For example, it has become evident that the intraocular pressure (internal pressure of the eye) of the eye to be treated, the progression of the curvature of the surface of the eye and the age of the patient may have an influence on the set/actual deviation. This applies equally to such factors as the intensity of a vacuum with which the suction ring is aspirated onto the eye, and—in the case of a mechanical flap-preparation system—the pressure with which the operating surgeon presses the handpiece, containing the cutting head, of the microkeratome system against the eye. It will be understood that numerous further factors may play a role in the set/actual deviation of the flap that is generated: in the case of a mechanical flap-preparation system, for example the frequency of oscillation of the cutting blade contained in the cutting head or/and the rate of feed of the cutting head or, in the case of a laser-assisted flap-preparation system, the pulse energy or the pulse repetition rate of the laser radiation that is being utilised for cutting the flap, or certain parameters of a scanner that is being utilised for local guidance of the laser radiation, or data of a camera that is being utilised for recording images of the eye of the patient. For the operating surgeon it is particularly difficult that the concrete influence of each individual factor is not readily apparent and, without other aids for the operating surgeon, is barely predictable.

It is the object of the invention to furnish an operating surgeon with an auxiliary tool that facilitates for him/her the preparation of a mechanical or laser-assisted LASIK operation, in particular the configuration of a flap-preparation system that is being utilised for the purpose of generating the flap. To be understood by the term 'LASIK' in this connection within the scope of the invention are both interventions in which the flap is cut into the stroma of the cornea and also interventions in which a purely epithelial flap is cut which does not extend into the stroma. The latter variant is frequently also designated as Epi-LASIK. Generally, however, the invention is suitable for any surgical methods in which a corneal flap is generated by means of a mechanical cutting instrument or by means of laser radiation. Furthermore, the auxiliary tool made available by the invention is also suitable for eye-surgery preparation systems with which keratoplasty treatments or lens treatments can be carried out on the human eye.

With a view to achieving the above object, the invention proposes, according to one aspect, a device for assisting in the preparation of an operation on the human eye for the purpose of generating a corneal flap by means of a mechanical or laser-assisted flap-preparation system, the device including:
  an input interface arrangement that permits the input of data relating to a set value of at least one flap parameter and also to at least one patient-related parameter,
  a computer that has been set up to access a stored data collection of several surgical data records, each of which includes a post-operative actual value of at least one flap parameter, a value for at least one patient-related parameter and configuration data of the flap-preparation system, the computer having been set up to ascertain, on the basis of the data collection in a manner depending on the input data, configuration information that represents a proposed configuration of the flap-preparation system,
  an output interface arrangement for outputting the configuration information to a user.

The configuration information that is output to the respective user via the output interface arrangement, which, for example, may include a monitor or/and a printer, can be ascertained by the computer on the basis of a statistical evaluation of the data collection or of at least a part of the same. In the case of a mechanical flap-preparation system the configuration proposal represented by the configuration information may include, for example, specifications relating to at least one of the following configuration parameters of the flap-preparation system: a size of a suction ring to be mounted onto the eye, a size of a cutting head of the flap-preparation system, the intensity of a suction-ring vacuum, a rate of feed of the cutting head, a frequency of oscillation of a cutting blade of the cutting head, and a feed distance of the cutting head. In the case of a laser-assisted flap-preparation system the configuration information may include, for example, specifications relating to at least one of the following configuration parameters of the flap-preparation system: a size of a suction ring to be mounted onto the eye, the intensity of a suction-ring vacuum, a pulse energy of a pulsed laser radiation serving for flap preparation, a pulse repetition rate of the laser radiation, a setting angle of at least one optical element, at least one scan parameter for a laser radiation of the flap-preparation system, a divergence angle of the laser radiation. In order that the computer can ascertain proposal values relating to parameters of such a type, the configuration data of each surgical data record expediently include specifications relating to at least one of these configuration parameters.

The basis for the configuration proposal ascertained by the computer is constituted by the data that have been input via the input interface arrangement. The input interface arrangement may, for example, enable an input of these data by the user and may for this purpose include, for example, a keyboard, a voice-input device, a graphical user interface, a pointer device (e.g. mouse) or elements of such a kind. As an alternative to an input of the data by the user, it is conceivable that the data are supplied by wireless or wire-bound transmission. For this purpose the input interface arrangement may include a suitable communications interface for receiving the data.

The input interface arrangement preferentially permits the input of data relating to at least one of the following flap parameters: a flap diameter, a flap thickness, a dimension or/and position of a flap hinge, an ellipticity of the flap, a decentring of the flap, a marginal-incision angle of the flap. In this connection each surgical data record expediently includes a post-operative actual value of at least one of these flap parameters.

With regard to the patient-related parameters, the input interface arrangement preferentially permits the input of data relating to at least one of the following patient-related parameters: a patient age, an intraocular pressure, at least one measure of the curvature of the anterior surface of the cornea, a corneal thickness, and a type of a measuring process employed for measuring the corneal thickness. Here too, once again it is advisable if each surgical data record includes a value of at least one of these patient-related parameters.

Various measuring techniques for measuring the corneal thickness are known in the state of the art. A common technique for corneal-thickness measurement (with which, incidentally, the thickness of a flap prepared in the cornea can also be measured) is ultrasonic pachymetry; another is reflectometry using low-coherence radiation, abbreviated to OLCR (this stands for optical low-coherence reflectometry). In the case of the latter method it is a question of an optical-coherence interferometric measuring process that causes an emitted measuring beam to interfere with a reflection beam reflected on the eye. Now it has become evident that different measuring techniques in the case of a given cornea may lead to different measured values for the cornea thickness, even though these differences may be slight. On account of such differences in the results of measurement it may be expedient to insert into the surgical data records a field in which the type of the measuring process being used is indicated. In the course of ascertaining its configuration proposal, the computer can then take into account which measuring process served as the basis for the value for the corneal thickness that was input via the input interface arrangement.

In a preferred design the computer has been set up to configure at least a part of the flap-preparation system in accordance with the configuration information, preferentially after receipt of a confirmation of the proposed configuration that has been input by the user via the input interface arrangement. For example, the computer can cause a prompt to be output, together with the configuration proposal, via the output interface arrangement that invites the operating surgeon to confirm the proposed configuration. Via the input interface arrangement the operating surgeon can then input a confirmation, for instance by clicking by means of a pointer device on a confirmation field superimposed on a monitor. It is also conceivable that the user is given the possibility of modifying the output configuration proposal in accordance with his/her wishes and subsequently of confirming it. At least a part of the configuration information confirmed by the operating surgeon can be utilised by the computer for the purpose of configuring the flap-preparation system automatically. A prerequisite for this is that the computer is coupled with such automatically configurable components of the flap-preparation system. For example, the computer may have been coupled with a central control unit of the flap-preparation system which controls the drive of a vacuum-pump arrangement for generating a suction-ring vacuum, the drive of a cutting head, the drive of a cutting blade or/and the pulse energy of a laser radiation. To the extent that the configuration information relates to parameters such as, for example, the intensity of the suction-ring vacuum, a frequency of oscillation of a cutting blade, a rate of feed or/and a feed distance of a cutting head or/and a pulse energy of laser radiation, it is conceivable that the values for these parameters contained in the configuration proposal are passed by the computer directly to the central control unit, so that the operating surgeon does not himself/herself have to input the corresponding values manually via suitable operating elements of the central control unit.

Other parts of the flap-preparation system may, on the other hand, be configurable by the operating surgeon manually in accordance with the configuration information, for example the suction ring to be used or/and a cutting head to be used or/and the pulse repetition rate of a laser radiation. In this regard the operating surgeon may, for example, have a choice among several suction rings of varying size, among several cutting heads of varying size or/and among several different pulse repetition rates. It is then incumbent on the operating surgeon to select, in accordance with the presets of the configuration proposal, a suitable suction ring, a suitable cutting head or/and a suitable pulse repetition rate.

The computer has preferentially been set up to generate a new surgical data record by using at least a part of the configuration information, at least a part of the input data and a post-operative actual value, input via the input interface arrangement, of at least one flap parameter. In this way the data collection can grow with each operation; the more extensive it becomes, the more reliable are the configuration proposals that the computer can provide, i.e. the more reliably can a configuration of the flap-preparation system be ascertained by the computer that permits the desired target values of the flap parameters to be obtained post-operatively with sufficient accuracy. In particular, it is conceivable either to assemble for each operating surgeon his/her own data collection or to insert a field into each surgical data record, into which specifications concerning the respective operating surgeon can be entered. In this way, in the course of the ascertainment of the configuration proposal the individual influence of the operating surgeon can be taken into consideration.

For the evaluation of the data collection the computer may have been set up to select, in a manner depending on the input data, a subgroup of data records from the surgical data records contained in the data collection and to ascertain the configuration information on the basis of the selected subgroup.

The computer may have been set up to ascertain, for at least a fraction of the data-record elements contained in the selected data records, a mean value and/or a standard deviation within the selected subgroup.

In addition to the ascertainment and output of a configuration proposal, in a preferred further development the computer may have been set up to evaluate statistically the data contained in the data collection and to bring about the visual output of a result of evaluation via the output interface arrangement. For example, the result of evaluation may include at least one representation of a frequency distribution of a post-operative actual value of a flap parameter. Alternatively or in supplement, the result of evaluation may include at least one representation of a value distribution of an element of the surgical data records as a function of at least one other element of the surgical data records. On the basis of the representation of such results of evaluation, the operating surgeon can, for example, gain an impression of the historical range of variation of the post-operative values of a certain flap parameter in a manner depending on defined boundary conditions. For example, he/she can also estimate with which probability under given boundary conditions a desired target value of a flap parameter can be obtained post-operatively.

According to a further aspect, the invention provides a process for preparing an operation on the human eye for the purpose of generating a corneal flap by means of a mechanical or laser-assisted flap-preparation system, including:

providing a stored data collection of several surgical data records, each of which includes a post-operative actual value of at least one flap parameter, a value for at least one patient-related parameter and configuration data of the flap-preparation system, receiving data relating to a set value of at least one flap parameter and also to at least one patient-related parameter via an input interface arrangement, accessing the data collection and ascertaining configuration information on the basis of the data collection in a manner depending on the input data, the configuration information representing a proposed configuration of the flap-preparation system, outputting the configuration information via an output interface arrangement.

This process can be carried out, in particular, by using a device of the type described above.

According to a preferred design, the process may include the steps of the receiving of a confirmation by the user of the proposed configuration via the input interface arrangement, and also of the automatic configuring of at least a part of the flap-preparation system in accordance with the configuration information in a manner depending on the receipt of the confirmation.

In the case of a mechanical flap-preparation system the automatic configuring may include an automatic setting of at least one of the following parameters of the flap-preparation system in accordance with the configuration information: an intensity of a suction-ring vacuum, a rate of feed of a cutting head, a frequency of oscillation of a cutting blade of the cutting head, and a feed distance of the cutting head.

In the case of a laser-assisted flap-preparation system, the automatic configuring may, on the other hand, include, for example, an automatic setting of at least one of the following parameters of the flap-preparation system in accordance with the configuration information: an intensity of a suction-ring vacuum, a pulse energy of a pulsed laser radiation serving for flap preparation, a pulse repetition rate of the laser radiation.

The process may further include selecting a suction ring from several suction rings of varying size in accordance with the configuration information and also equipping the flap-preparation system with the selected suction ring.

Similarly, in the case of a mechanical flap-preparation system the process may include selecting a cutting head from several cutting heads of varying size in accordance with the configuration information and also equipping the flap-preparation system with the selected cutting head.

The invention will be elucidated further in the following on the basis of the appended drawings. Represented are.

Figure 1:
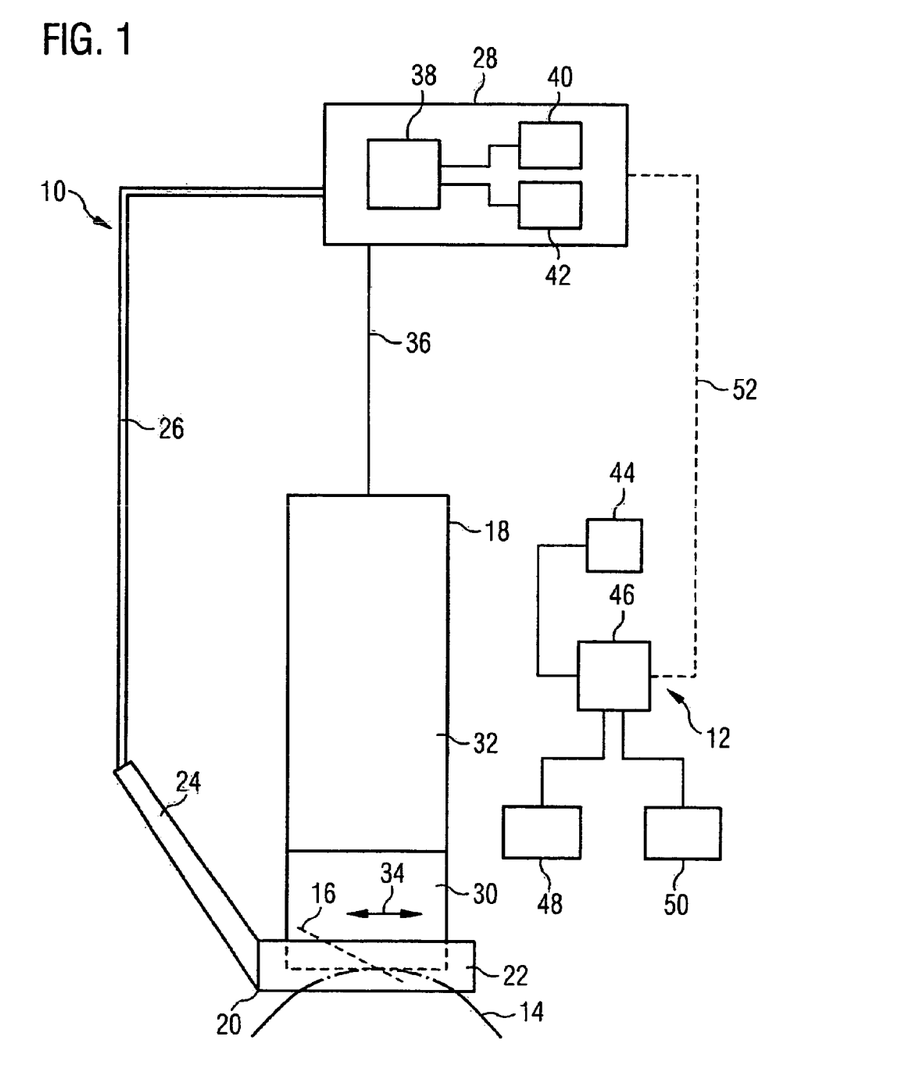
FIG. 1 a schematic synoptic representation of a mechanical flap-preparation system (microkeratome system) and of a device that assists an operating surgeon in the ascertainment of a suitable configuration of the microkeratome system, according to an exemplary embodiment, FIG. 2 a schematic sketch that illustrates various sequences in connection with the configuration of a microkeratome system and implementation of a surgical intervention using the microkeratome system, according to an exemplary embodiment, FIG. 3a,b schematically, various steps in the ascertainment of a proposal for a configuration of the microkeratome system according to an exemplary embodiment and FIGS. 4a, 4b exemplary forms of output for results of a statistical analysis of the data contained in a data collection of the device according to FIG. 1.

Reference will firstly be made to FIG. 1. This shows—in greatly simplified, schematic form—an exemplary embodiment of a microkeratome system 10 and also of a device 12 that serves to assist the operating surgeon working with the microkeratome system 10 in the ascertainment of a suitable configuration for the microkeratome system 10.

The microkeratome system 10 is employed by the operating surgeon within the scope of a LASIK treatment (a term by which, within the scope of this disclosure, the Epi-LASIK variant is also to be covered) in order to generate a corneal flap on a human eye 14 to be operated on. For this purpose the microkeratome system 10 includes a handpiece 18, exchangeably equipped with a cutting blade 16, and also a suction-ring unit 20, which in the exemplary case shown is formed separately from the handpiece 18, with a suction ring 22 to be mounted onto the eye 14. Said suction ring is, for example, integrally connected to at least one connecting piece 24 which includes, in a manner not represented in any detail but known as such, one or more evacuation ducts which are connected to a corresponding number of evacuation chambers (likewise not represented in any detail) formed in the suction ring 22. At least one evacuation chamber of such a type serves for aspirating the suction ring 22 onto the eye 14.

Onto the connecting piece 24 at least one hose line 26 is capable of being attached which in turn is capable of being attached to a central control console 28—constructed, for example, as a bench instrument—of the microkeratome system 10. The control console 28 contains a vacuum-pump arrangement which is not represented in any detail (with one or more vacuum pumps, which may optionally have varying pump capacity), by means of which a vacuum is capable of being generated in each evacuation chamber of the suction ring 22 via the at least one hose line 26.

The handpiece 18 exhibits a cutting head 30, serving as carrier for the cutting blade 16, and also a motorised drive unit 32 which is detachably coupled with the rutting head 30. The cutting head 30 is supported, guided in a linear direction of motion, by guide structures, not represented in any detail, which are formed on the suction ring 22. For example, the guide structures may include two toothed tracks formed on the suction ring 22 and spaced from one another, in which two pinions arranged on the cutting head 30 and in driving communication with the drive unit 32 engage in intermeshing manner. In this way a linear reciprocating motion of the cutting head 30 relative to the suction ring 22 is possible. This reciprocating motion of the cutting head 30 is illustrated in FIG. 1 by a double-headed arrow 34.

The cutting blade 16 is, in turn, received in the cutting head 30 in laterally mobile manner, in which connection 'lateral' means a direction perpendicular to the direction of motion 34 of the cutting head 30 (i.e. perpendicular to the plane of the drawing in FIG. 1). For the purpose of lateral oscillation, the cutting blade 16 is also in driving communication with the drive unit 32.

For the purpose of driving the cutting head 30 and the cutting blade 16 the drive unit 32 may contain a single drive motor (electric motor) or separate motors. A solution with separate motors is shown, for example, in EP 1 757 253 A1; with regard to a one-motor solution, reference may be made, for example, to EP 0 442 156 A1.

Via a cable 36 the handpiece 18 is connected to the control console 28. Located in the cable 36 are one or more electrical lines, via which the drive unit 32 is supplied with electrical operating power and, where appropriate, electrical control signals.

Contained in the control console 28 is a microprocessor-based control unit 38 which operates in accordance with a control program contained in a memory 40. The control unit 38 controls the operation of the handpiece 18 (more precisely, the operation of the drive unit 32) and preferentially also the operation of the aforementioned vacuum-pump arrangement. The control console 28 may in addition be constructed with a manually operable input unit 42, for instance in the form of a touch-screen, via which the operating surgeon can input set values for various operating parameters of the microkeratome system 10. Such operating parameters are, for example, intensity of the aspirating vacuum with which the suction ring 22 is aspirated onto the eye 14, the frequency of oscillation of the cutting blade 16, the rate of feed of the cutting head 30 and, where appropriate, the length of the feed displacement of the cutting head 30 (feed distance). The latter parameter determines the location of the flap hinge within the peripheral line of the flap, i.e. the spacing of the hinge line from this peripheral line.

For the operating surgeon there is the problem of finding a suitable configuration of the microkeratome system 10 that enables preset target values for the flap thickness, the flap diameter and the location of the flap hinge in a given patient to be obtained in the best way possible. The cause of this problem is that the post-operative actual values of these flap parameters may often deviate from corresponding nominal values or setting values of the microkeratome system. To give one example, a cutting head with a nominal incision depth of 120 μm does not necessarily result in a post-operative flap thickness of exactly the same value. Instead of this, the post-operative flap thickness may easily be a few μm greater or smaller than the nominal value of 120 μm. The same also applies, for example, to the flap diameter, the post-operative actual value of which may easily be a few tenths of a millimeter smaller or greater than a specified nominal value of the suction ring 22. The influences that result in such deviations may be variable. The operating surgeon himself/herself may be one influencing factor, inasmuch as he/she, for example, presses the handpiece 18 with more or less strong pressure against the suction ring 22 and hence against the eye 14. The patient may also be an influencing factor, namely via such patient-specific parameters as the age of the patient, the thickness of the cornea of the eye to be treated and the internal pressure of the eye to be treated. Because the various influencing factors are frequently not correlated with one another in a manner that is unequivocally discernible for the operating surgeon, for the operating surgeon it is difficult to predict which configuration of the microkeratome system 10 is the right one in order to be able actually to realise with sufficient precision defined target values for a flap to be generated.

In order to facilitate the suitable configuration of the microkeratome system 10 for the operating surgeon, the device 12 is provided. The latter includes a data collection (database) 44 saved in memory, in which surgical data records have been saved or can be saved which in each instance have been assigned to a corneal operation. The data collection 44 is open in the sense that after every operation which has been carried out a further surgical data record can be created and added to the existing data collection.

The data collection 44 is managed by a computer 46 that has been programmed to evaluate the data collection 44 statistically and to output corresponding results of evaluation on an output device (e.g. printer, monitor) 48. It will be understood that several such output devices 48 of like or different type may be attached to the computer 46. All the output devices 48 constitute together an output interface arrangement in the sense of the invention. Furthermore, the computer 46 has been programmed to receive data that, for example, are input by the operating surgeon via an input device 50 and that relate to a forthcoming operation. These input data relate, inter alia, to values of various patient-specific parameters such as, for instance, the age of the patient, the thickness of the cornea to be treated, the intraocular pressure (IOP) and at least one measure of the curvature of the corneal surface (so-called K-value). In addition, the input data specify desired target values for various flap dimensions that are to be achieved in the case of the flap to be generated. The flap dimensions in question are preferentially the flap diameter, the flap thickness, and the location of the flap hinge (expressed, for example, as the spacing of the hinge line from the nearest tangent to the peripheral line of the flap).

It will be understood that the computer 46 may have been connected to several input devices 50 which, for example, may be of varying type (e.g. keyboard, voice-input module, pointer device). Each input device 50 is part of an input interface arrangement in the sense of the invention.

The computer 46 has been set up by programming to ascertain a configuration proposal for the microkeratome system 10 on the basis of the data collection 44, taking the input data into consideration, and to output corresponding configuration information on the output device 48. The configuration information preferentially contains specifications concerning a suction-ring size, a cutting-head size, a frequency of oscillation for the rutting blade 16, a rate of feed for the cutting head 30, a feed distance for the cutting head 30, and also the intensity (level) of the aspirating vacuum for the suction ring 22. The specifications relating to the suction-ring size or/and to the cutting-head size may, for example, be numerical figures that specify in concrete terms a proposed size of the suction ring 22 or of the suction head 30. Alternatively, it is conceivable that the specifications relating to the suction-ring size or/and to the cutting-head size include a type designation of the suction ring 22 or of the cutting head 30, provided that the type designation can be assigned unambiguously to a certain nominal size of the suction ring 22 or of the cutting head 30.

For the ascertainment of the configuration proposal, the computer 46 examines the data collection 44 in order to establish, on the basis of the historical data saved therein, which configuration of the microkeratome system 10 is best suited in order to achieve the target values, input via the input device 50, of the various flap dimensions with sufficient accuracy under the boundary conditions of the values, likewise input via the input device 50, of the various patient-specific parameters. The configuration proposal that is output on the output device 48 then has to be confirmed by the operating surgeon, namely by an appropriate input on the input device 50. Where appropriate, the computer 46 can permit the operating surgeon to modify the proposed configuration, for which purpose the operating surgeon likewise has to undertake corresponding inputs via the input device 50. As soon as the operating surgeon has confirmed a particular configuration displayed on the output device 48, the computer 46 generates in the data collection 44 a new surgical data record into which at least a part of the configuration data of the confirmed configuration is written. In addition, the computer 46 writes at least a part of the patient-specific parameter values into the newly generated surgical data record. The surgical data record is later supplemented by post-operatively measured values of the flap diameter, of the flap thickness and, where appropriate, of the hinge location, it being possible for these measured values to be input, for example, by the operating surgeon via the input device 50. Alternatively, it is conceivable that the computer 46 is connected to a measuring apparatus that is used for measuring these flap dimensions, so that the measured values can be routed to the computer 46 without intervention of the operating surgeon and can be written from there into the data collection 44.

As soon as the operating surgeon has accepted a particular configuration of the microkeratome system 10, he/she selects from an available assortment of cutting heads of varying size a cutting head with the suitable size and incorporates it into the handpiece 18. He/she also selects a suitable suction ring from an available assortment of suction rings of varying size. The remaining parameters to be configured of the microkeratome system (e.g. intensity of the aspirating vacuum, frequency of oscillation, rate of feed, feed distance) may, according to one design, be capable of being input into the control console 28 manually by the operating surgeon via the input unit 42. According to another design, it is conceivable that, after confirmation of a configuration proposal, the configuration parameters in question are communicated immediately to the control console 28 by the computer 46. This possibility is represented in FIG. 1 by a dashed connecting line 52 between the computer 46 and the control console 28. The control console 28 can then accept the communicated parameter values and can convert them into corresponding control signals.

In the representation shown in FIG. 1 the device 12 and the control console 28 are shown as components that are separate from one another. It will, of course, be understood that the computer 46, the data collection 44 and, where appropriate, also the output device 48 or/and the input device 50 (or at least parts thereof) may have been integrated into the control console 28 in modular manner. In such a case it will be understood that the input unit 42 and the input device 50 do not have to be provided separately from one another but may instead merge to form a common input unit.

Figure 2:
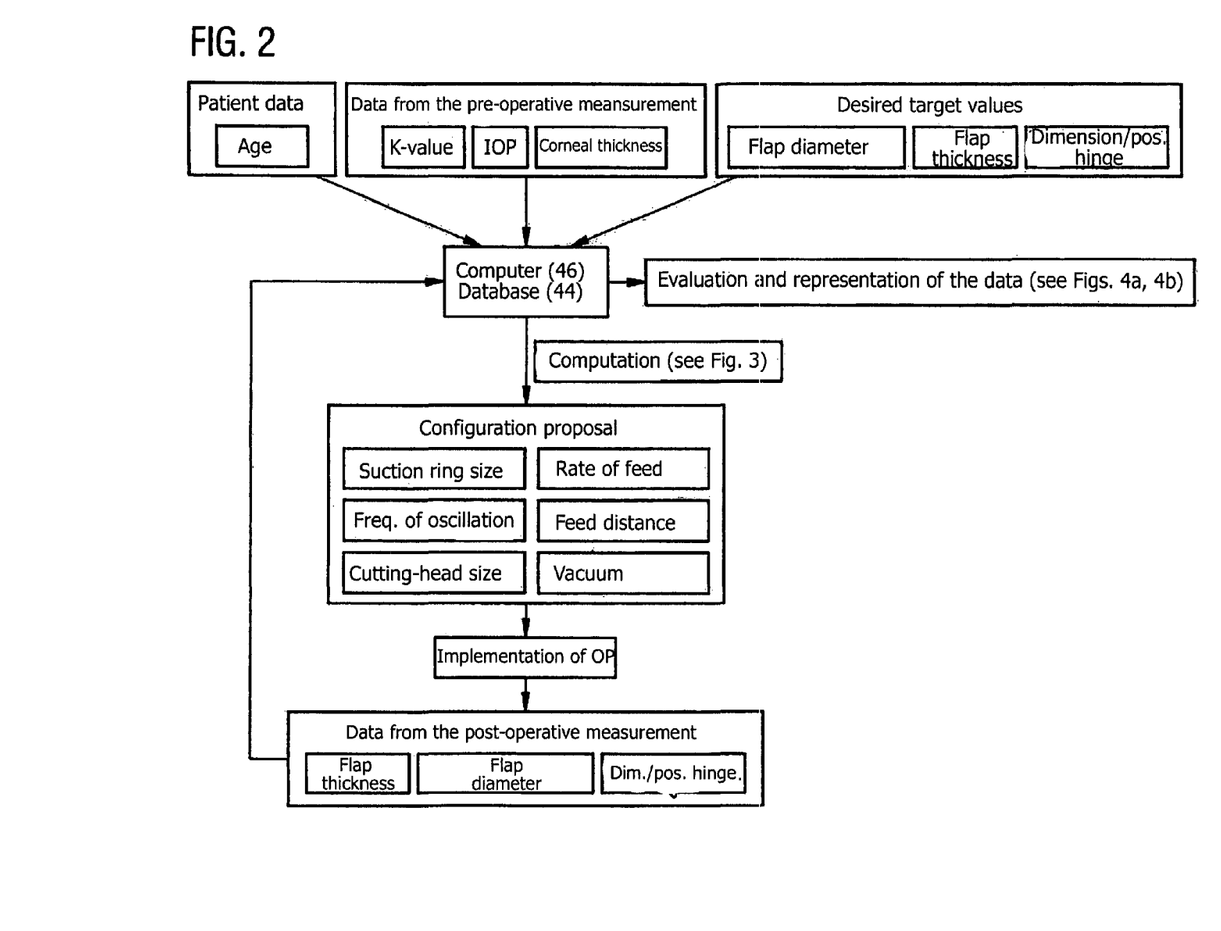

FIG. 2 illustrates the sequences described so far in connection with the configuration of the microkeratome system 10, in the form of a block representation. The starting-point is the input of patient data, of data from a pre-operative measurement and of desired target values into the computer 46 of the device 12. In the concrete exemplary case the patient data relate to the age of the patient to be treated, the pre-operative measured data include a K-value, the intraocular pressure IOP and also the corneal thickness, and the desired target values relate to the flap diameter, the flap thickness and the hinge spacing (hinge location). The input of these data into the computer 46 is illustrated in FIG. 2 by corresponding arrows.

For the input data the computer 46 then computes, by accessing the surgical data records contained in the database 44, a configuration proposal which in the exemplary case shown includes specifications relating to the suction-ring size, to the frequency of oscillation, to the cutting-head size, to the rate of feed, to the feed distance and to the intensity of the aspirating vacuum of the suction ring 22. It will be understood that this listing of parameters that may be contained in the configuration proposal is neither definitive nor restrictive.

After the microkeratome system has been configured in the manner proposed by the computer 46, the operating surgeon carries out the planned operation. Subsequently, by means of a suitable measuring apparatus the generated flap is gauged as regards its thickness, its diameter and the hinge location (hinge spacing). The post-operative measured data obtained in this way are thereupon fed into the database 44, at least in part, either automatically or by the operating surgeon, and are written therein into a surgical data record assigned to the operation in question.

Figure 3A:
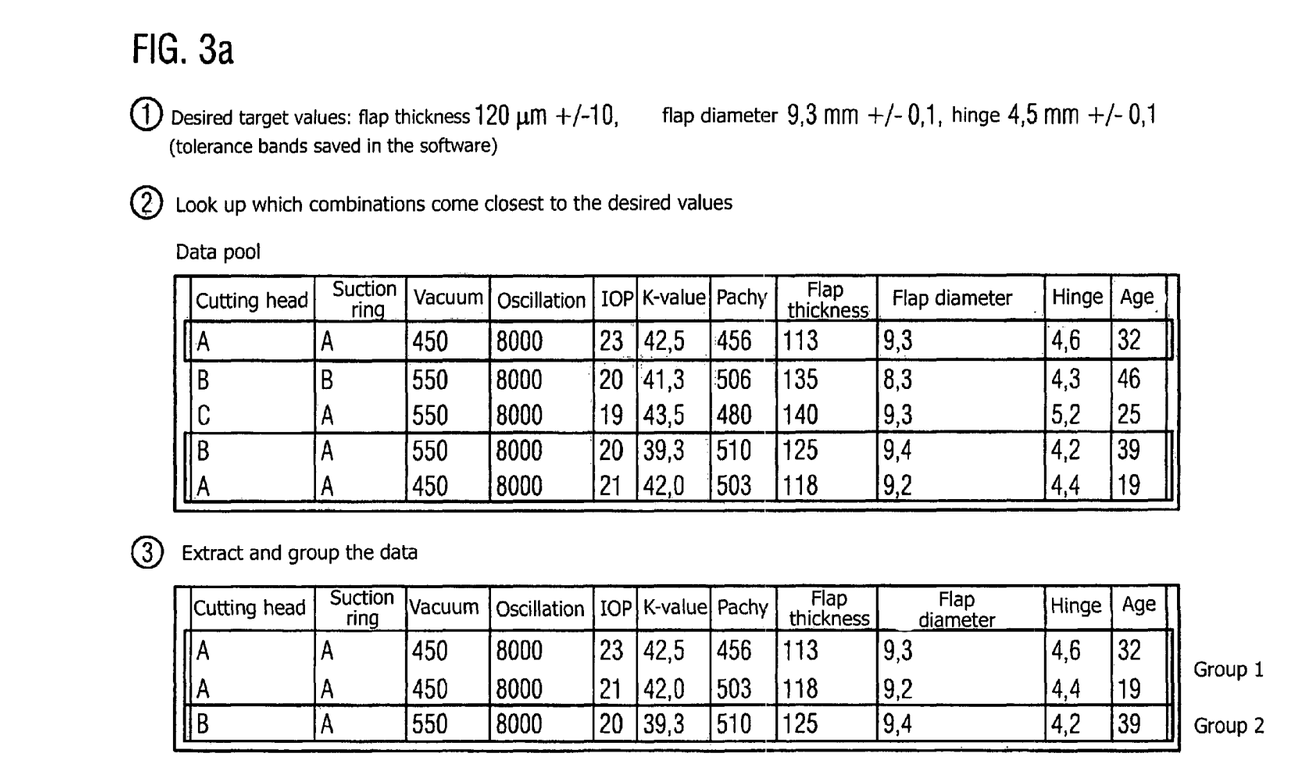
Figure 3B:
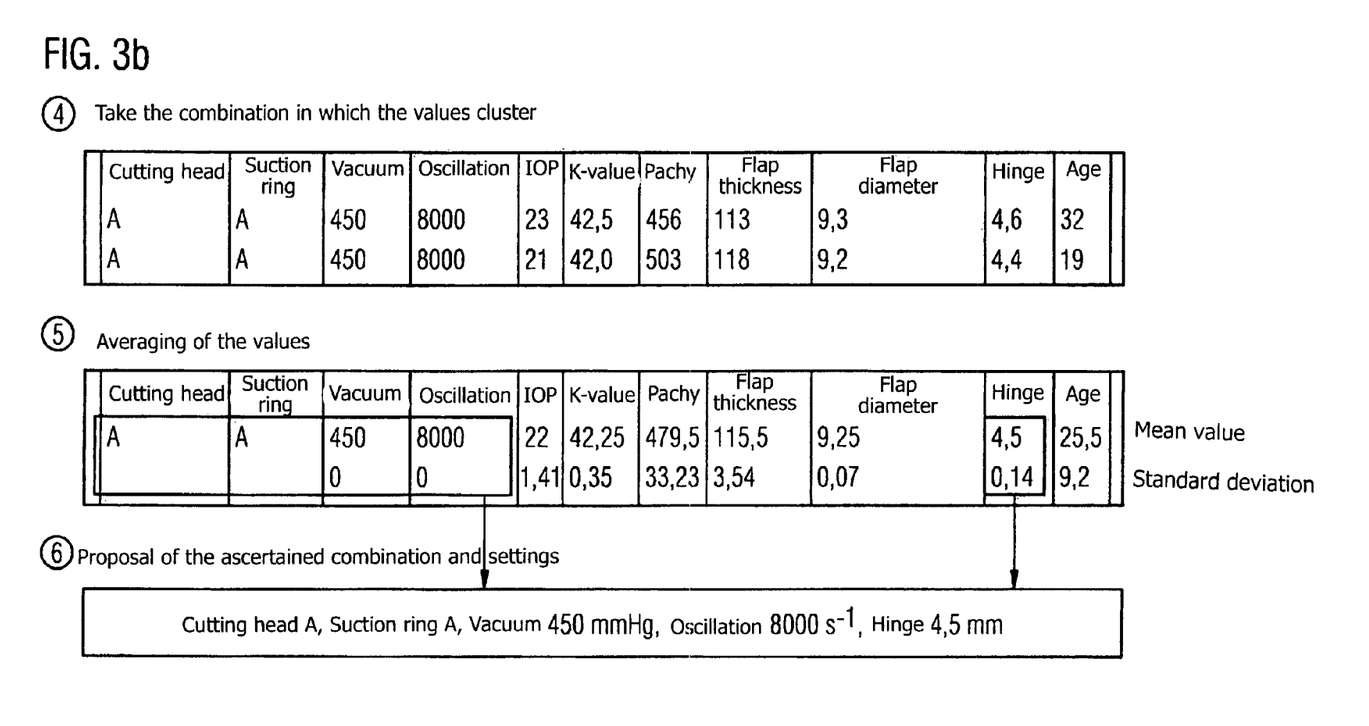

For more detailed elucidation of exemplary sequences in connection with the computation of the configuration proposal, reference will now be made to FIG. 3a,b. Therein six steps (1) to (6) are represented, one underneath the another, which can be carried out in this order by the computer 46.

In a step (1) the computer 46 receives the desired target values for the various flap dimensions, here a target value of 120 µm for the flap thickness, a target value of 9.3 mm for the flap diameter, and a target value of 4.5 mm for the hinge length. The tolerance bands specified in FIG. 3a in the case of step (1) are saved in the control program of the computer 46, so they do not have to be input separately by the operating surgeon. It will be understood that in an alternative design the permissible tolerances can be input by the operating surgeon himself/herself.

In a step (2) the computer accesses the database 44 and examines the surgical data records contained therein with regard to which of these data records comes, or come, closest to the preset target values. For the purpose of illustration, in FIG. 3a in the case of step (2) a data pool with a total of five surgical data records stored therein is shown. Each of these surgical data records contains fields for a plurality of data-record elements, in which connection, in the exemplary case shown, fields for data-record elements Cutting head, Suction ring, Vacuum, Oscillation, IOP, K-Value, Pachy, Flap thickness, Flap diameter, Hinge and Age are contained. The data-record elements Cutting head and Suction ring relate to the cutting-head size and the suction-ring size, respectively; the parameter values A, B, C entered in this regard into the data-record fields represent varying sizes of the cutting head and of the suction ring.

The data-record element Vacuum relates to the reduced pressure that is generated for the purpose of fixing the suction ring 22 to the eye 14, the data-record element Oscillation relates to the frequency of oscillation of the cutting blade 16. The data-record elements IOP, K-Value and Pachy relate to the internal pressure of the eye, to the curvature of the anterior surface of the cornea, and to the corneal thickness. The next two data-record elements Flap thickness and Flap diameter specify the post-operative actual values of these two parameters. The data-record element Hinge specifies the post-operatively measured value for the hinge length, and the data-record element Age specifies the age of the patient.

Within the scope of the examination of the stored surgical data records the computer establishes in step (2) that the first, fourth and fifth data records come closest to the target values input in step (1). This is illustrated in FIG. 3a by these three data records being framed.

In the subsequent step (3) the computer 46 subdivides the data records previously selected in step (2) into groups, to be specific depending upon similarity to the target values that were input in step (1). In exemplary manner, in FIG. 3a in the case of step (3) two groups of data records are represented, a group 1 with a total of two data records and a group 2 with a total of one data record. It is readily discernible that the data records contained in group 1 satisfy the target values input in step (1) with regard to their values for the flap thickness, the flap diameter and the hinge location, taking the permissible tolerances into consideration. On the other hand, the data record of group 2 does not satisfy these target values, because the value for the hinge spacing (4.2 mm) in this record lies outside the permissible range (as shown by the tolerance specification ±0.1 mm in step (1), the permissible range for the hinge length amounts to 4.4 mm to 4.6 mm).

In the subsequent step (4) the computer 46 therefore establishes that the two data records of group 1 are to be drawn upon for the subsequent ascertainment of the configuration proposal.

In a subsequent step (5) the computer 46 computes from the data records selected in step (4) a mean value and also a standard deviation for each data-record element.

The computed mean values for the cutting-head size, for the suction-ring size, for the intensity of the aspirating vacuum, for the frequency of oscillation of the cutting blade and for the hinge location are then combined by the computer 46 in a step (6) so as to form a configuration proposal and are communicated to the operating surgeon (e.g. by output on a monitor). In the exemplary case shown in FIG. 3b the configuration proposal comprises a cutting head of size A, a suction ring of size A, an aspirating vacuum of 450 mm Hg, a frequency of oscillation of the cutting blade of $8000 \ s^{-1}$, and a hinge dimension (corresponding to the feed distance of the cutting head) of 4.5 mm.

In addition to the computation of a configuration proposal, the computer 46 is programmed to evaluate the data contained in the database 44 statistically and to represent corresponding results of evaluation graphically on the output device 48. For example, the computer 46 may have been programmed to ascertain the historical value distribution of a particular parameter (e.g. of the post-operative flap thickness) under given boundary conditions (e.g. use of a cutting head of size A in the case of an aspirating vacuum of the suction ring 22 of 450 mm Hg and a K value of the eye being treated between 41.0 mm Hg and 43.0). An exemplary output format for such a frequency distribution is shown in FIG. 4a, the parameter for which the frequency distribution holds being denoted by x.

Alternatively or additionally, the computer 46 may have been programmed, for example, to generate and to output dependency diagrams that illustrate the value combinations that have occurred historically of two or more parameters (e.g. flap diameter, flap thickness) under given boundary conditions (e.g. cutting head of size A, suction ring of size A, vacuum of 450 mm Hg, K value between 41.0 mm Hg and 43.0). An exemplary output format of such a dependency diagram is shown in FIG. 4b. The variables x, y therein represent the parameters, the historical value combinations of which are to be represented in the diagram.

Figure 4A:
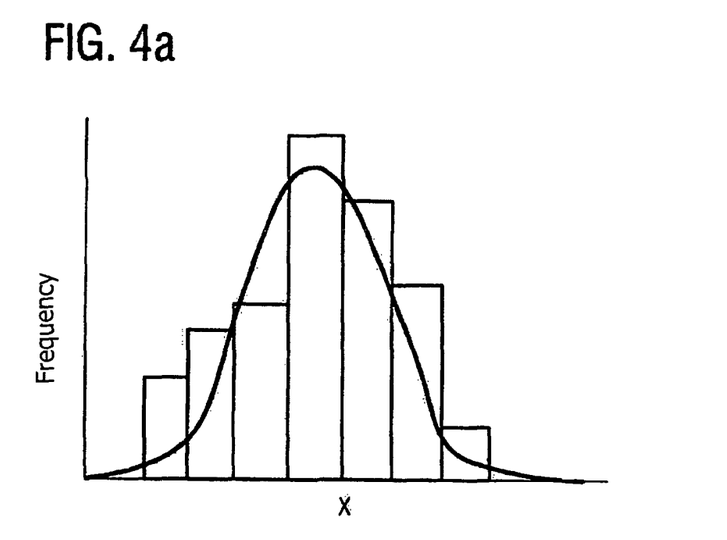
Figure 4B:
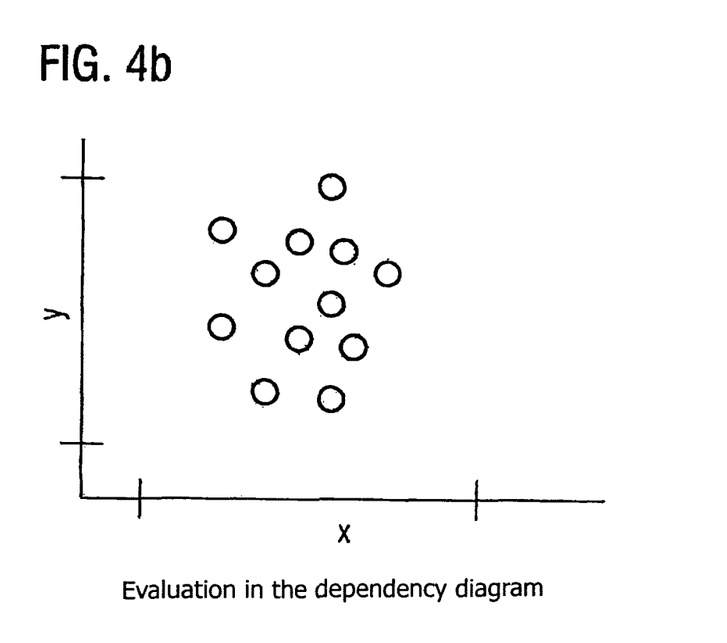

From representations such as FIG. 4a and FIG. 4b the operating surgeon can gain insights into the various influencing factors that may result in the set/actual deviations, described above, of the flap dimensions. In this way the operating surgeon is furnished with a useful tool in order to improve the planning and implementation of the operation.

So far within the scope of the elucidation of the Figures the starting-point was a mechanical flap-preparation system—that is to say, a microkeratome system. According to the methodology presented here, however, a flap-preparation system for the generation of a corneal flap by laser technology is equally capable of being configured. Compared to a microkeratome system, in the case of a laser-assisted flap-preparation system at least a fraction of the flap parameters, with respect to which the operating surgeon or user can input set values pre-operatively, may be different. For example, in the case of a laser-assisted flap-preparation system it is conceivable that, inter alia, set values for an ellipticity of the flap (that is to say, the extent of a deviation from an ideal circular shape), for a decentring of the flap or/and for a marginal-incision angle of the flap can be input. The marginal-incision angle designates the angle at which a lateral incision defining the flap margin ascends in the direction towards the corneal surface from a bed incision defining the stromal bed of the flap. Here (at least in a levelled, i.e. applaned, state of the cornea) a right angle or an obtuse angle may be chosen, for example. In the latter case the lateral incision (marginal incision) runs obliquely outwards proceeding from the bed incision. The decentring of the flap is designated by a specification concerning the offset of the flap in relation to a preset reference point of the eye, for example the apex of the anterior surface of the cornea.

The configuration information that is output by the computer by way of configuration proposal in the case of a laser-assisted flap-preparation system may also differ, at least partly, from that in the case of a mechanical flap-preparation system. Thus the configuration information in the case of a laser-assisted flap-preparation system may, for example, contain, inter alia, specifications relating to a pulse energy or/and to a pulse repetition rate of the laser radiation that is being utilised for the purpose of generating the flap. The configuration information may alternatively or additionally contain specifications relating, for example, to the wavelength of the laser radiation, to the pulse length of the laser pulses of the laser radiation, to the room temperature or/and to the incision depth (i.e. flap thickness).

Alternatively or additionally, the configuration information may contain specifications relating to a setting angle of at least one optical element of the flap-preparation system, to at least one scan parameter or/and to a divergence angle of the laser radiation. The laser-assisted flap-preparation system may, for example, contain at least one optical element in the beam path of the laser radiation that is adjustable as regards angular measure, for instance a diffractive optical element which, depending upon the setting angle, may have a varying influence on one or more laser parameters such as, for instance, the pulse energy, the pulse length or the pulse repetition rate. The setting angle of such an optical element may relate, for example, to the location of the optical axis of the element in relation to the direction of propagation of the laser radiation, this angle being capable of being changed by a suitable actuator (e.g. actuated by electric motor, piezoelectrically or magnetically). By way of scan parameter (i.e. setting parameter of a scanner being utilised for local control of the radiation focus of the laser radiation), a scan rate, a spot spacing (i.e. the local spacing of two consecutive focus locations), a scan-line spacing (i.e. the spacing of adjacent lines in a scan pattern, according to which the radiation focus is moved by means of the scanner) or/and scaling factors for the x-direction, y-direction or/and z-direction enter into consideration, for example. According to conventional notation, in this connection the z-direction is to designate the direction of propagation of the laser radiation, whereas the x-direction and the y-direction designate two directions that span a plane orthogonal to the z-direction. Ordinarily the scanner will include suitable components in order to enable both a longitudinal local control of the focus (that is to say, in the z-direction) and a transverse local control of the radiation focus (i.e. in the x-y plane). The depth of the treatment plane is linked via the z-scaling factor with the associated setting value for the location of the treatment plane, whereas such parameters as the flap diameter, the hinge length and the hinge location are linked to one another via the x-scaling and y-scaling. The spot spacing is determined, in turn, from the scan rate and the pulse repetition rate. As far as the treatment plane is concerned, by this term the incision depth is meant. It can be set via the divergence angle of the laser radiation. A greater incision depth may, for example, be set by using diffractive optics that can change the divergence of the radiation, for example by suitable control of the phase shift.

The invention claimed is:

1. A device for assisting a laser-assisted flap-preparation system in generating a corneal flap, the device including:
an input interface arrangement that permits the input of data relating to a target value of at least one flap parameter and to at least one patient-related parameter;
a computer that has been set up to:
access a stored data collection of a plurality of surgical data records, each record including a post-operative actual value of at least one flap parameter, a value for at least one patient-related parameter, and configuration data of the flap-preparation system;
select at least two of the records that have post-operative actual values of at least one flap parameter that most closely match the target value of at least one flap parameter;
ascertain configuration information from the configuration data of the at least two records, the configuration information representing a proposed configuration of the flap-preparation system most likely to yield the the target value of at least one flap parameter; and
configure at least a part of the flap-preparation system in accordance with the configuration information.

2. The device according to claim 1, wherein:
the input interface arrangement permits the input of data relating to at least one of the following flap parameters: a flap diameter, a flap thickness, a dimension or/and a position of a flap hinge, an ellipticity of the flap, a decentring of the flap, a marginal-incision angle of the flap; and
each surgical data record includes a post-operative actual value of at least one of these flap parameters.

3. The device according to claim 1, wherein:
the input interface arrangement permits the input of data relating to at least one of the following patient-related parameters: a patient age, an intraocular pressure, at least one measure of the curvature of the anterior surface of the cornea, a corneal thickness, and a type of a measuring process employed for measuring the corneal thickness; and
each surgical data record includes a value of at least one of these patient-related parameters.

4. The device according to claim 1, wherein:
the configuration information includes specifications relating to at least one of the following configuration parameters of the flap-preparation system: a size of a suction ring to be mounted onto the eye, the intensity of a suction-ring vacuum, a pulse energy of a pulsed laser radiation serving for flap preparation, a pulse repetition rate of the laser radiation, a wavelength of the laser radiation, a pulse length of the laser radiation, a room temperature, an incision depth, a setting angle of at least one optical element, at least one scan parameter for a laser radiation of the flap-preparation system, a divergence angle of the laser radiation; and
the configuration data of each surgical data record include specifications relating to at least one of these configuration parameters.

5. The device according to claim 1, wherein the computer has been set up to configure at least a part of the flap-preparation system after receipt of a confirmation of the proposed configuration that has been input by the user via the input interface arrangement.

6. The device according to claim 1, wherein the computer has been set up to generate a new surgical data record by using at least a part of the configuration information, at least a part of the input data and a post-operative actual value, input via the input interface arrangement, of at least one flap parameter.

7. The device according to claim 1, wherein the computer has been set up to ascertain, for at least a fraction of the data record elements contained in the selected data records, a mean value or/and a standard deviation within the selected subgroup.

8. A method for assisting a laser-assisted-flap preparation system in generating a corneal flap, comprising:
accessing a stored data collection of a plurality of surgical data records, each of record including a post-operative actual value of at least one flap parameter, a value for at least one patient-related parameter, and configuration data of the flap-preparation system;
receiving data relating to a set target value of at least one flap parameter and to at least one patient-related parameter via an input interface arrangement;
selecting at least two of the records that have post-operative actual values of at least one flap parameter that most closely match the target value of at least one flap parameter;
ascertaining configuration information from the configuration data of the at least two records, the configuration information representing a proposed configuration of the flap-preparation system most likely to yield the target value of at least one flap parameter; and
automatically configuring at least a part of the flap-preparation system in accordance with the configuration information.

9. The method according to claim 8, further including:
receiving a confirmation by the user of the proposed configuration of the flap-preparation system via the input interface arrangement.

10. The method according to claim 9, wherein the automatic configuring includes an automatic setting of at least one of the following parameters of the flap-preparation system in accordance with the configuration information:
an intensity of a suction-ring vacuum, a pulse energy of a pulsed laser radiation serving for flap preparation, a pulse repetition rate of the laser radiation, a wavelength of the laser radiation, a pulse length of the laser radiation, a room temperature, an incision depth.

11. The method according to claim 8, further including:
selecting a suction ring from several suction rings of varying size in accordance with the configuration information; and
equipping the flap-preparation system with the selected suction ring.

12. The method according to claim 8, wherein the configuration information includes specifications relating to at least one of the following configuration parameters of the flap-preparation system:
a size of a suction ring to be mounted onto the eye, the intensity of a suction-ring vacuum, a pulse energy of a pulsed laser radiation serving for flap preparation, a pulse repetition rate of the laser radiation, a wavelength of the laser radiation, a pulse length of the laser radiation, a room temperature, an incision depth, a setting angle of at least one optical element, at least one scan parameter for a laser radiation of the flap-preparation system, a divergence angle of the laser radiation.

13. The device according to claim 1, further comprising:
an output interface arrangement for outputting the configuration information to a user.

14. The method according to claim 8, further comprising:
outputting the configuration information to a user via an output interface arrangement.

15. The device according to claim 13, wherein the computer has been set up to evaluate statistically the data contained in the data collection and to bring about the visual output of a result of evaluation via an output interface arrangement.

16. The device according to claim 15, wherein the result of evaluation includes at least one representation of a frequency distribution of a post-operative actual value of a flap parameter.

17. The device according to claim 15 or 16, wherein the result of evaluation includes at least one representation of a value distribution of an element of the surgical data records as a function of at least one other element of the surgical data records.

* * * * *